United States Patent [19]

Abts

[11] 4,381,674
[45] May 3, 1983

[54] ULTRASONIC DETECTING AND IDENTIFYING OF PARTICULATES

[75] Inventor: Leigh R. Abts, Providence, R.I.

[73] Assignee: Micro Pure Systems, Inc., Smithfield, R.I.

[21] Appl. No.: 276,038

[22] Filed: Jun. 22, 1981

[51] Int. Cl.³ .......................................... G01N 29/00
[52] U.S. Cl. .................................... 73/599; 73/61 R; 73/432 PS
[58] Field of Search ................ 73/599, 61 R, 432 PS, 73/861.25, 200

[56] References Cited

U.S. PATENT DOCUMENTS

| | | | |
|---|---|---|---|
| 3,553,636 | 1/1971 | Baird | 73/599 |
| 3,710,615 | 1/1973 | Johnson et al. | 73/61 R |
| 3,779,070 | 12/1973 | Cushman et al. | 73/432 PS |
| 3,816,773 | 6/1974 | Baldwin et al. | 73/61 R |
| 3,914,984 | 10/1975 | Wade | 73/599 |
| 4,112,773 | 9/1978 | Abts | 73/61 R |
| 4,237,720 | 12/1980 | Abts | 73/19 |

Primary Examiner—Anthony V. Ciarlante

[57] ABSTRACT

A method of detecting and identifying particulates in the recirculating fluid flow for an oil recovery system by counting the number of ultrasonic pulses reflected from the particulates and comparing the number counted with the amount of attenuation of ultrasonic energy across the flow.

9 Claims, 5 Drawing Figures

ULTRASONIC DETECTING AND IDENTIFYING OF PARTICULATES

FIELD OF THE INVENTION

This invention relates to a method of detecting and identifying particulates in an oil recovery system.

BACKGROUND OF THE INVENTION

In secondary oil recovery systems, oil is recovered by pumping water into the ground through a secondary hole near the oil deposit. The water seeps through the ground, and as it is under pressure, the water forces the oil to the surface through a primary drill hole. This oil flow, however, will contain oil, water and solid particles. Most of the oil is separated from the rest of the flow at the surface, and the residual liquid is recirculated back into the ground through the secondary drill hole. The use of this residual water substantially reduces the amount of fresh or sea water which must be continually added while the system is in operation.

The principal drawback of this method is that the solid particles will be carried by the residual water back into the secondary drill hole, and they may be large enough to block the seepage holes in the ground thereby preventing the water from reaching the oil deposit. Due to the very small size of the particles which would cause such a blockage, conventional filtering has been unable to correct the problem. An alternative solution has been to shut down the system until the water can be satisfactorily cleaned. However, conventional particle detection methods are not useful in determining when to shut down, as the recirculated flow also contains oil droplets, which would be simultaneously detected. While the droplets do not otherwise adversely affect the system, the prior art detectors cannot discriminate between the solid particles and the droplets, and the presence of the droplets confuses and makes meaningless any readings that are made.

Further, the recirculated flow may also contain large oil slugs, the presence of which indicates that the oil-water separator devices are not functioning properly. Accordingly, it is desirable to detect these slugs as well.

SUMMARY OF THE INVENTION

I have discovered that solid particles in a recirculating flow for an oil recovery system can be identified by using an ultrasonic transmitter means to send ultrasonic energy beams across the flow, separate reflections being received from all the particulates, which reflections are then counted and the count compared with the amount of attenuation of the beam caused by the flow, the comparison giving the percentage of particulates which are solid particles. The size of the solid particles is determined by selecting appropriate threshold voltages when counting the reflections.

In preferred embodiments, a pair of transducers are mounted across from each other, and the attenuation of the ultrasonic energy sent between them is measured. At the same time, a transmitting-receiving transducer is mounted nearby to count the total particulate reflections. As the presence of oil substantially increases the amount of db attenuation, a comparison of the amount of attenuation with the number of detected particulates gives the percentage of solid particles detected. Size information is obtained by the amount of threshold voltage for the transmitting-receiving transducer. Increasing this voltage increases the minimum size of the particulates which can be detected so that the number of particulates can be counted for a range of sizes around the critical particle size and the percentage of solid particles for each size determined.

PREFERRED EMBODIMENT

We turn now to the structure and operation of a preferred embodiment, after first briefly describing the drawings.

Drawings

Structure

Figure 1:
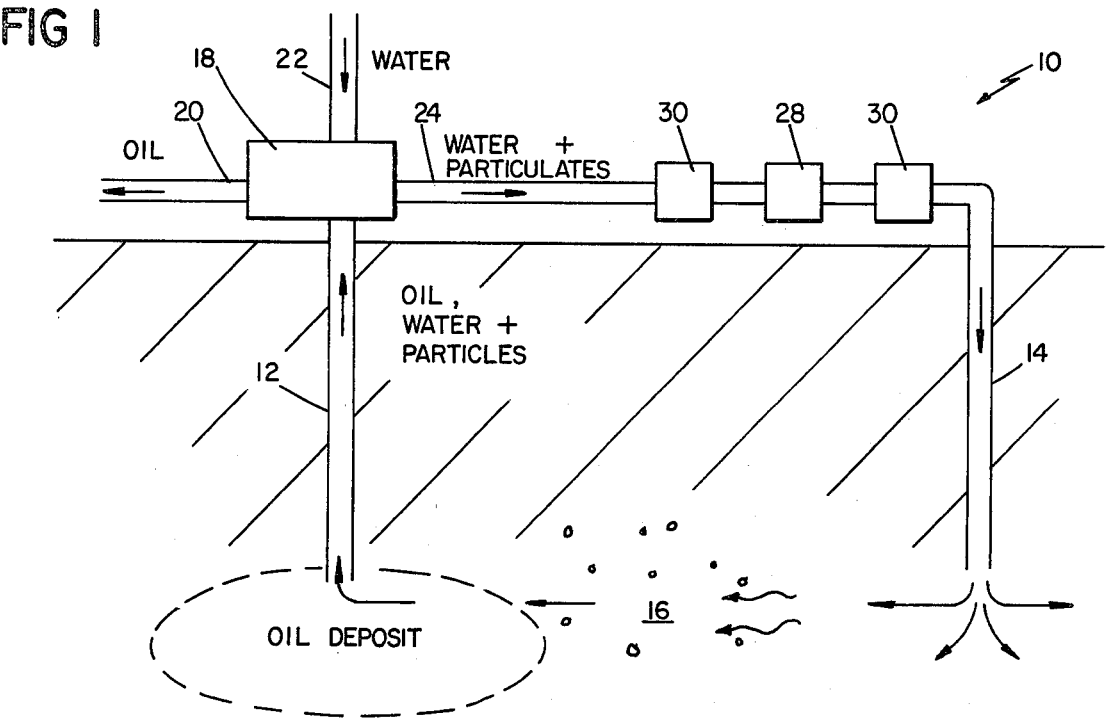
FIG. 1 is a cross-sectional view of an oil recovery system with this invention.

Referring to FIG. 1, there is shown a secondary oil recovery system at 10. System 10 comprises a primary drill hole 12 which extends into the oil deposit and a secondary drill hole 14, which is nearby. The lower end of secondary drill hole 14 is separated from the oil deposit by a ground seepage area 16.

The surface end of the primary drill hole 12 is connected to a separator unit 18. Separator unit 18 also has an oil output pipe 20, a water input pipe 22 and a connector pipe 24. Input pipe 22 draws water, preferably seawater, into the system. The connector pipe 24 goes to the secondary drill hole 14, and it contains two identical detectors 30 on either side of a filter 28.

Figure 2:
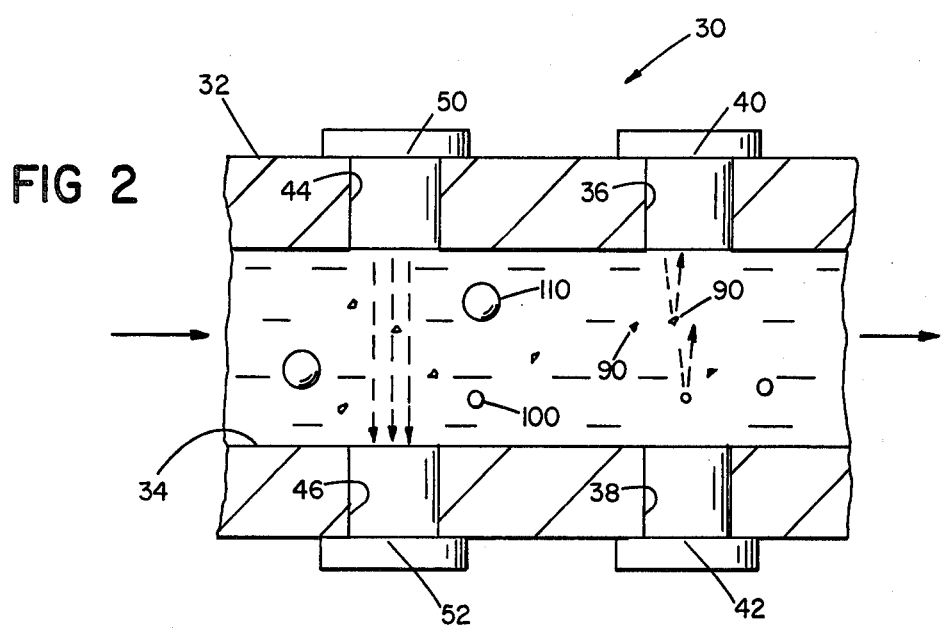
FIG. 2 is a cross-sectional view of the detector of this invention.

One of the ultrasonic detectors 30 is shown in FIG. 2. The detector 30 comprises a tube 32 of methyl methacrylate having an interior bore 34. The tube 32 has a first pair of holes 36, 38, which are disposed 180° apart. A first pair of ultrasonic transducers 40, 42 are located in holes 36, 38. The transducers 40, 42 are all of the type described in my U.S. Pat. application, Ser. No. 187,615, filed Sept. 15, 1980, incorporated herein by reference. The detector 30 also has a second pair of holes 44, 46, which are identical to the first pair 36, 38 and which have a second pair of ultrasonic transducers 50, 52 mounted therein. The transducers 50, 52 are identical to the first pair except that they use 3 MHz crystals, while the transducers of the first pair use 10 MHz crystals. As also shown in FIG. 2, normal flow through the bore 34 contains solid particles 90, and oil droplets 100, and it may contain some large oil slugs 110.

Figure 3:
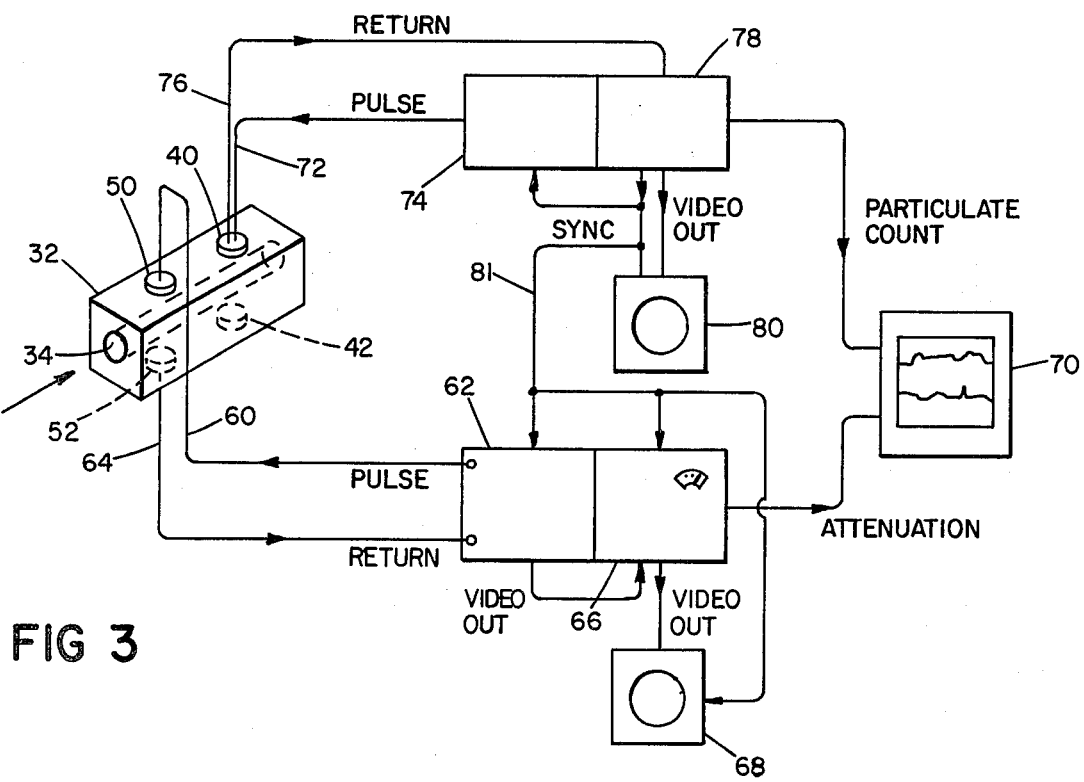
FIG. 3 is a block diagram of the electronic circuit used with this invention.

As shown in FIG. 3, lead 60 connects the pulse output of pulser-receiver 62 to transducer 50. A second lead 64 connects transducer 52 to the receive input of pulser-receiver 62. Pulser-receiver 62 is connected to an absorption monitor 66, the outputs from which go to an oscilloscope 68 and a 2-channel analog recorder 70. The pulser-receiver 62 and the absorption monitor 66 are an MPH 1150 and an MPA 1700 respectively, both available from Micro Pure Systems, Inc., the assignee of this application. The oscilloscope 68 is a Tektronix 465B oscilloscope, and the analog recorder 70 is a Houston Instruments OMNISCRIBE Model B5117-5.

As for the first pair of transducers 40, 42, transducer 42 is not connected in the preferred embodiment. Transducer 40, however, is connected to leads 72, 76. Lead 72 is from the pulse output of amplifier 74, and lead 76 is connected to the receive input for amplifier 78. The outputs from amplifier 78 go to oscilloscope 80 and analog recorder 70. Also, a sync pulse lead 81 is connected from oscilloscope 80 to the pulser-receiver 62, the absorption monitor 66, the oscilloscope 68 and the amplifier 78. Amplifier 74 is an MPH 1150, and amplifier 78 is an MCM 1100A, both available from Micro Pure Systems, Inc. The oscilloscipe 80 is the same as oscilloscope 68.

OPERATION

In operation, water is drawn into the system 10 through inlet pipe 22, and this water is pumped through connector pipe 24 to the secondary drill hole 14. At the bottom of hole 14, the water seeps under pressure into the ground. Some of this water passes through the area 16 between the pipe 14 and the oil deposit. For the usual earth formation of concern, the seepage area 16 in the vicinity of an oil deposit has small passageways of about $10\mu$ diameter. When the water reaches the oil deposit, the water pressure forces some of the oil up through the primary drill hole 12 and to the separator unit 18. This flow, however, also contains water and solid particles picked up by the water and oil. The separator unit 18 separates oil from the rest of the flow, and recovered oil is then pumped from outlet pipe 20. The remainder of the flow, which now is primarily water with oil droplets 100 and solid particles 90, as shown in FIG. 2, is then fed back to the connecting pipe 24. The system 10, however, has a net water loss because water exits from the secondary drill hole in all directions and not all of it is recovered. Therefore, additional water, usually seawater if available, is pumped into the system from the inlet pipe 22 and added to the recovered flow going to the secondary drill hole 14. The additional water may also carry particulates. The filter 28 is able to remove the larger particles, but generally, more than a few parts per million of solid particles with diameters of one-third the diameter of the seepage holes or greater are objectionable, as they will block the seepage holes and prevent the water from reaching the oil deposit. Thus, in the usual case, particles with diameters of approximately $3\mu$ are the largest permitted. For the purposes of this measurement, one part per million would be 1 milligram by weight of solid particles of this size for each liter of fluid.

Figure 4:
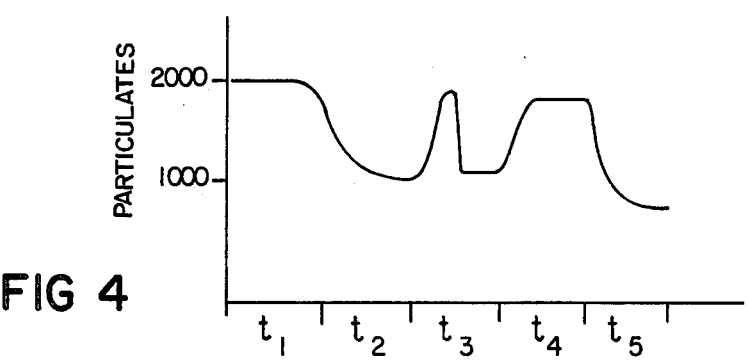
FIG. 4 is a representative particulate-count graph.

The detector 30 of this invention permits detection of an improper operating condition and allows the operators time to shut down the system until the water can be adequately cleaned. In the preferred embodiment, ultrasonic transducer 40 operates as in my U.S. Pat. application Ser. No. 187,615, filed Sept. 15, 1980. The transducer 40 acts as a transmitter-receiver and sends bursts of ultrasonic energy across the flow. It then counts the reflections from all the particulates. The total number of reflections for any given burst or period of time can be plotted or displayed on oscilloscope 80 and on one plot of analog recorder 70. A sample particulate-count plot is shown in FIG. 4. For time period $t_1$, a total of about 2000 reflections have been received, and this represents both solid particles and oil droplets. For the purpose of this example, the particular reading is made by using a threshold voltage of 17 mv for the transducer 40. In order to be detected, the reflection from a particulate must produce a signal with a voltage level above the threshold voltage. Accordingly, as larger particles produce a higher reflection voltage, there is a correlation between the threshold voltage and the minimum radius of the solid particles detected. This relationship is defined by the following formula:

$$R = A\sqrt[3]{mv} \ ;$$

if $KR<<1$ $$K = 2\pi f/c$$

where R is the particle radius; A is a constant of approximately 0.6, mv is the threshold voltage; c is the speed of sound; and f is frequency (10 MHz, for the preferred embodiment). The requirement that $KR<<1$ is met for the preferred embodiment.

Accordingly, for $t_1$ all 2000 particulates detected have a diameter equal to or greater than $3\mu$, the cutoff value. It should be noted that this equation does not yield a precise result for the oil droplets. The droplets have a fairly close impedance match with the water, and for a droplet and a solid particle of equal size, the reflection from the droplet is much weaker. The weaker signal will be interpreted as a reflection from a smaller particulate. Accordingly, for the example given, all the solid particles would have diameters of $3\mu$ or greater, but the smallest droplet would probably have a diameter of about 30.

For the above equation, the constant A is only an approximation. For example, if the solid particles were all coal, A would be 1.18. If they were glass, A would be 2.0. As the specific type of particle is not known, additional measurements are taken using threshold voltages slightly above and below the threshold voltage which would theoretically give according to the formula the cut-off diameter. For example, additional threshold voltages of 10 mv and 30 mv are selected. The particulates are counted for these threshold voltages, and the three readings together give a close approximation of the number of particulates at or above the particular critical diameter. Although these three measurements are taken sequentially, flow conditions change very gradually, and they can be considered to have been taken at the same instant.

Figure 5:
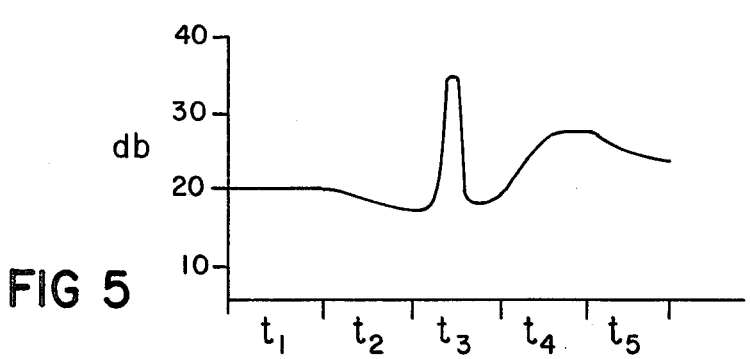
FIG. 5 is a representative attenuation graph.

For the same $t_1$, the ultrasonic transducers 50, 52 measure attenuation a few inches upstream. This reading is about 20 db for $t_1$, as shown in the graph of FIG. 5. The db reading is taken at the same time as the particulate count, as a sync pulse from the sync pulse lead 81 triggers both transducers 40, 50 simultaneously. Both plots, as represented by FIGS. 4 and 5, would be shown on the chart of the analog recorder 70. Also, the oscilloscopes 68, 80 would individually display the results, if desired. The low level of attenuation for this time period means that almost all of the particles detected are solid particles, and as revealed by the formula, all of these particles have diameters at or over the acceptable limit. For time $t_2$, the number of particulates has fallen to 1000, but the db attenuation has fallen slightly also. Thus, although there are fewer particulates in the flow, they are still mostly solid particles of a size large enough to block the seepage holes. Accordingly, for time periods $t_1$ and $t_2$, the system would be shut down until the water is purified. For time $t_3$, there is a spike on both graphs. The spike indicates the presence of a large oil slug, and as previously explained, that indicates a failure in the separator unit 18. If any more than one or two spikes are detected every few minutes, the system 10 would be shut down until the separator unit 18 is repaired. At time $t_4$, the particulate count is about 1800, but the db level has risen to about 28. This indicates that the vast majority of the particulates are oil droplets. Finally, for time $t_5$, the particulate count has dropped to 1000, but as the db level remains high, most of the particulates detected are oil droplets. The system could continue to operate for the conditions of $t_4$ and $t_5$. Of course, the graphs of FIGS. 4 and 5 are greatly compressed, and except for the spiking caused by the oil slugs, the changes shown would be far more gradual in reality.

The detectors 30 upstream and downstream of the filter 28 operate in the same manner. The use of both allows a comparison of the conditions before and after the filter, which will indicate how effectively the filter is operating.

OTHER EMBODIMENTS

In another embodiment of this invention, only one pair of transducers 40, 42 are used. In this configuration, transducer 40 receives reflections as before, but transducer 42 is connected, and it measures the attenuation of the unreflected portion of the beams. In this embodiment, the second pair of transducers 50, 52 is eliminated.

This method and apparatus may also be used with a tertiary oil recovers system in which chemicals are used instead of the recirculating water.

Other variations will occur to those skilled in the art. What I claim is:

1. A method of identifying solid particles in a flow in an oil recovery system comprising:
   sending ultrasonic pulses across the flow,
   detecting and counting the reflections of ultrasonic energy from particulates in the flow,
   comparing the number of reflections with the amount of attenuation of ultransonic pulses across the flow, thereby determining the percentage of particulates which are solid particles.

2. The method of claim 1 wherein sending ultrasonic pulses includes simultaneously sending a first ultrasonic pulse for obtaining the reflections and a second pulse for obtaining the amount of attenuation.

3. The method of claim 1 wherein sending ultrasonic pulses includes sending a pulse, a portion of which is reflected from the particulates in the flow and a portion of which is attenuated by the flow.

4. The method of claim 1 wherein comparing includes simultaneously displaying a plot of the number of reflections and a plot of db attenuation on chart of an analog recorder.

5. The method of claim 1 further comprising the step of setting a first threshold voltage for reflections so that only reflections from particulates having a diameter of or larger than a selected size are detected and counted.

6. The method of claim 5 further comprising setting additional threshold voltages and counting the reflections therefor, the additional threshold voltages being above and below the first threshold voltage.

7. A particulate identification apparatus comprising,
   means for transmitting an ultrasonic pulse into a flow containing particulates,
   means for receiving and counting reflected ultrasonic pulses from said particulates,
   means for measuring the attenuation of ultrasonic pulses across the flow, and
   means for comparing the number of counted pulses with the attenuation to determine the percentage of particulates which are solid particles.

8. The particulate identification apparatus of claim 7 wherein said means for measuring comprises a transducer on one side of a conduit and a receiving transducer on the opposite side of the conduit.

9. The particulate identification apparatus of claim 7 wherein said means for comparing comprises a two channel analog recorder, said recorder simultaneously displaying plots of counted reflection pulses and attenuation.

* * * * *